United States Patent
Barofsky et al.

(10) Patent No.: US 7,001,328 B1
(45) Date of Patent: Feb. 21, 2006

(54) METHOD FOR USING TROPOELASTIN AND FOR PRODUCING TROPOELASTIN BIOMATERIALS

(75) Inventors: Andrew D. Barofsky, Portland, OR (US); Kenton W. Gregory, 3737 SW. Council Crest Dr., Portland, OR (US) 97201

(73) Assignees: Kenton W. Gregory, Portland, OR (US); Providence Health Systems-Oregon, Seattle, WA (US)

( * ) Notice: Subject to any disclaimer, the term of this patent is extended or adjusted under 35 U.S.C. 154(b) by 599 days.

(21) Appl. No.: 08/797,770

(22) Filed: Feb. 7, 1997

Related U.S. Application Data (63) Continuation-in-part of application No. 08/658,855, filed on May 31, 1996, now Pat. No. 5,990,379, and a continuation-in-part of application No. 08/341,881, filed on Nov. 15, 1994, now Pat. No. 5,989,244.

(51) Int. Cl.
*A61F 2/02* (2006.01)
(52) U.S. Cl. .................................. 600/36; 623/23.72
(58) Field of Classification Search .............. 623/11, 623/23.72, 23.75; 600/36; 427/2.24, 2.25
See application file for complete search history.

(56) References Cited

U.S. PATENT DOCUMENTS

| | | | |
|---|---|---|---|
| 4,132,746 A | 1/1979 | Urry et al. | |
| 4,187,852 A | 2/1980 | Urry et al. | |
| 4,474,851 A * | 10/1984 | Urry .......................... | 428/373 |
| 4,500,700 A | 2/1985 | Urry | |
| 4,589,882 A | 5/1986 | Urry | |
| 4,693,718 A | 9/1987 | Urry et al. | |
| 4,721,096 A | 1/1988 | Naughton et al. | |
| 4,783,523 A | 11/1988 | Urry et al. | |
| 4,801,299 A | 1/1989 | Brendel et al. | |
| 4,870,055 A | 9/1989 | Urry et al. | |
| 4,886,062 A | 12/1989 | Wiktor .......................... | 623/1 |
| 4,960,423 A | 10/1990 | Smith ........................... | 623/1 |
| 4,963,489 A | 10/1990 | Naughton et al. | |
| 4,976,734 A | 12/1990 | Urry et al. | |
| 5,032,508 A | 7/1991 | Naughton et al. | |
| 5,064,430 A | 11/1991 | Urry | |
| 5,156,613 A * | 10/1992 | Sawyer ....................... | 128/898 |
| 5,160,490 A | 11/1992 | Naughton et al. | |
| 5,209,776 A | 5/1993 | Bass et al. | |
| 5,223,420 A | 6/1993 | Rabaud et al. | |
| 5,254,113 A | 10/1993 | Wilke | |
| 5,266,480 A | 11/1993 | Naughton et al. | |

(Continued)

FOREIGN PATENT DOCUMENTS

WO    WO 91/04073    4/1991

(Continued)

OTHER PUBLICATIONS

Ooyama et al, "Substratum-Bound Elastin Peptide Inhibits Aortic Smooth Muscle Cell Migration in Vitro", Arteriosclerosis 7(6):593-598 (1987).

(Continued)

*Primary Examiner*—Paul B. Prebilic
(74) *Attorney, Agent, or Firm*—Marger Johnson & McCollom, PC (57) ABSTRACT

It is a general object of the invention to provide a method of effecting repair or replacement or supporting a section of a body tissue using tropoelastin, preferably crosslinked tropoelastin and specifically to provide a tropoelastin biomaterial suitable for use as a stent, for example, a vascular stent, or as conduit replacement, as an artery, vein or a ureter replacement. The tropoelastin biomaterial itself can also be used as a stent or conduit covering or coating or lining.

2 Claims, 3 Drawing Sheets

U.S. PATENT DOCUMENTS

| | | | |
|---|---|---|---|
| 5,292,362 A * | 3/1994 | Bass et al. | 106/124 |
| 5,336,256 A | 8/1994 | Urry | |
| 5,336,616 A | 8/1994 | Livesey et al. | |
| 5,428,014 A * | 6/1995 | Labroo et al. | 514/12 |
| 5,443,550 A | 8/1995 | Yoneda et al. | |
| 5,460,939 A | 10/1995 | Hansbrough et al. | |
| 5,478,739 A | 12/1995 | Slivka et al. | |
| 5,510,254 A | 4/1996 | Naughton et al. | |
| 5,512,475 A | 4/1996 | Naughton et al. | |
| 5,516,680 A | 5/1996 | Naughton et al. | |
| 5,516,681 A | 5/1996 | Naughton et al. | |
| 5,518,915 A | 5/1996 | Naughton et al. | |
| 5,571,181 A * | 11/1996 | Li | 623/11 |
| 5,591,224 A | 1/1997 | Schwartz et al. | 623/1 |
| 5,607,475 A | 3/1997 | Cahalan et al. | 623/11 |
| 5,628,785 A * | 5/1997 | Schwartz et al. | 623/11 |
| 5,968,096 A * | 10/1999 | Whitson et al. | 623/15 |
| 5,989,244 A * | 11/1999 | Gregory et al. | 606/8 |
| 5,990,379 A * | 11/1999 | Gregory et al. | 623/11 |
| 6,087,552 A * | 7/2000 | Gregory | 623/11 |
| 6,110,212 A * | 8/2000 | Gregory | 623/23.72 |

FOREIGN PATENT DOCUMENTS

| | | | |
|---|---|---|---|
| WO | WO/91/04073 | | 4/1991 |
| WO | 9614807 | * | 5/1996 |

OTHER PUBLICATIONS

Rabaud et al, "Soluble Fibrinogen Derivatives Generated by Thrombin: Affinity for Elastin", Thrombosis Research 43:205-211 (1986).

Pool et al, "Production of High-Potency Concentrations of Antihemophilic Giobulin in a Closed-Bag System", The New England Journal of Medicine 273(27):1443-1447 (1965).

Landsman et al, "Light-absorbing properties, stability, and spectral stabilization of indocyanine green", Journal of Applied Physiology 40(4):575-583 (1976).

Crissman, Robert S., "Comparision of Two Digestive Techniques for Preparation of Vascular Elastic Networks for SEM Observation", Journal of Electron Microscopy Technique 6:335-348 (1987).

Guisti et al, "Bioartificial Polymeric Materials: A New Method to Design Biomaterials by using both Biological and Synthetic Polymers", TRIP 1(9):261-267 (1993).

Debra Bedell-Hogan, Philip Trackman, William Abrams, Joel Rosenbloom, Herbert Kagan. "Oxidation, Cross-Linking, and Insolubilization of Recombinant Tropoelastin by Purified Lysyl Oxidase", (Journal of Biological Chemistry, vol. 268, No. 14, pp. 10345-10350 (1993).

Guisti et al, "Bioartificial Polymeric Materials: A New Method to Design Biomaterials by using both Biological and Synthetic Polymers". TRIP 1(9): 261-267 (1993).

Ooayama et al, "Substratum-Bound Elastin Peptide Inhibits Aortic Smooth Muscle Cell Migration in Vietro" Arteriosclerosis 7(6):593-598 (1987).

* cited by examiner

Coacervation:

METHOD FOR USING TROPOELASTIN AND FOR PRODUCING TROPOELASTIN BIOMATERIALS

This is a Continuation-in-Part of U.S. Ser. No. 08/341,881, filed Nov. 15, 1994, now U.S. Pat. No. 5,989,244, and a Continuation-in-Part of U.S. Ser. No. 08/658,855, filed on May 31, 1996, now U.S. Pat. No. 5,990,379.

This invention was made with Government support under Grant No. DAMD17-96-1-6006 awarded by U.S. Army Medical Research Acquisition Activity. The U.S. Government has certain rights in the invention.

BACKGROUND OF THE INVENTION

This invention relates to a method for using tropoelastin, and more particularly to a method for producing tropoelastin biomaterials.

Elastic fibers are responsible for the elastic properties of several tissues such as skin and lung, as well as arteries, and are composed of two morphologically distinct components, elastin and microfibrils. Microfibrils make up the quantitatively smaller component of the fibers and play an important role in elastic fiber structure and assembly.

The most abundant component of elastic fibers is elastin. The entropy of relaxation of elastin is responsible for the rubber-like elasticity of elastic fibers. In vertebrates elastin is formed through the secretion and crosslinking of tropoelastin, the 72-kDa biosynthetic precursor to elastin. This is discussed, for example, in an article entitled "Oxidation, Cross-linking, and Insolubilization of Recombinant Crosslinked Tropoelastin by Purified Lysyl Oxidase" by Bedell-Hogan, et al in the Journal of Biological Chemistry, Vol. 268, No. 14, on pages 10345–10350 (1993).

In vascular replacement and repair, the best current option is to implant autologous veins and arteries where the obvious limit is the supply of vessels which can be sacrificed from the tissues they were intended to service. Autologous vein replacements for damaged arteries also tend to be only a temporary measure since they can deteriorate in a few years in high pressure arterial circulation.

When autologous graft material is not available, the surgeon must choose between sacrificing the vessel, and potentially the tissue it sub-served, or replacing the vessel with synthetic materials such as Dacron or Gore-tex. Intravascular compatibility indicate that several "biocompatible polymers", including Dacron, invoke hyperplastic response, with inflammation particularly at the interface between native tissue and the synthetic implant. Incomplete healing is also due, in part, to a compliance mismatch between currently used synthetic biomaterials and native tissues.

Thirty to forty percent of atherosclerotic stenoses that are opened with balloon angioplasty restenose as a result of ingrowth of medial cells. Smooth muscle ingrowth into the intima appears to be more prevalent in sections of the artery where the internal elastic lamina (IEL) of the artery is ripped, torn, or missing, as in severe dilatation injury from balloon angioplasty, vessel anastomoses, or other vessel trauma that results in tearing or removal of the elastic lamina.

Prosthetic devices, such as vascular stents, have been used with some success to overcome the problems of restenosis or re-narrowing of the vessel wall resulting from ingrowth of muscle cells following injury. However, metal stents or scaffolds being deployed presently in non-surgical catheter based systems to scaffold damaged arteries are inherently thrombogenic and their deployment can result in catastrophic thrombotic closure. Metal stents have also been well demonstrated to induce a significant intimal hyperplastic response within weeks which can result in restenosis or closure of the lumen. Optimal arterial reconstruction would restore the arterial architecture such that normal vascular physiology and biology would be re-established thus minimizing acute and long-term maladaptive mechanisms of vascular homeostasis. Until relatively recently, the primary methods available for securing a prosthetic material to tissue (or tissue to tissue) involved the use of sutures or staples. fibrin glue, a fibrinogen polymer polymerized with thrombin, has also been used (primarily in Europe) as a tissue sealant and hemostatic agent.

Damage to the arterial wall through disease or injury can involve the endothelium, internal elastic lamina, medial smooth muscle and adventitia. In most cases, the endogenous host response can repair and replace the endothelium, the smooth muscle and the adventitial layers over a period of weeks to months depending upon the severity of the damage. However, elastin does not undergo extensive postdevelopmental remodelling and the capacity for elastin synthesis declines with age. (see "Regulation of Elastin Synthesis in Organ and Cell Culture" by Jeffrey M. Davidson and Gregory C. Sephel in Methods in Enzymology 144 (1987) 214–232. Therefore, once damaged, elastic fibers are not substantially reformed. Neosynthesis of elastin in arterial walls subject to hypertension or neointimal hyperplasia represents the most significant example of post developmental elastin synthesis. This synthesis results in elastic structures mostly composed of elastin fibrils whose organization is unlike normal elastin architecture and probably contributes little to the restoration of normal vascular physiology.

In animal models of intimal hyperplasia or atherosclerosis it is well accepted that disruption of the internal elastic lamina is a prerequisite to reliable production of intimal hyperplasia or atherogenesis in large animals or primates. see Schwartz R. S., et al, in an article entitled "Restenosis After Balloon Angioplasty: Practical Proliferation Model In Porcine Coronary Arteries" in Circulation 1990: 82: 2190–2200. This observation is supported by several lines of evidence that suggest a role for elastin in the biological regulation of several cell types. Pathological studies indicate that elastin provides a secure attachment for endothelial cells and can act as a barrier to macromolecules such as mitogens and growth factors preventing these molecules from entering the media of blood vessels. Lipids, foamy macrophages, and other inflammatory cells do not appear to enter the intima as readily when a substantial and continuous elastin membrane is present immediately to the endothelium according to Sims, F. H., et al, in an article entitled "The Importance of A Substantial Elastic Lamina Subjacent To The Endothelium In Limiting the Progression of Atherosclerotic Changes" in Histopathology (1993) at 23:307–317. In addition, it has been shown by Ooyama, Toshiro and Sakamoto that chemotactic effects of soluble elastin peptides and platelet derived growth factor are inhibited by substratum bound elastin peptides. see "Elastase in the Prevention of Arterial Aging and the Treatment of Atherosclerosis." see "The Molecular Biology and Pathology of Elastic Tissues" edited by Chadwick, Derek J. and Jamie A. Goode, John Wiley and Sons Ltd, Chichester, England (1995). In vitro experiments show that alpha elastin suppresses the phenotypic transition (contractile to synthetic) of rabbit arterial SMC by interacting with a 130 kDa cell surface elastin binding protein for cell binding sequence VGVAPG. Rabbit smooth muscle cells adhering to elastic fibers appears to favor the contractile over the synthetic state which is identified with restonotic responses to injury. see "Changes in Elastin Binding Proteins During Phenotypic Transition of Rabbit Arterial Smooth Muscle Cells in Primary Culture" by Yamamoto, et al in Experimental Cell Research 218 (1995) pg. 339–345. Similar work by Ooyama and colleagues has demonstrated that the phenotypic change of smooth muscle cells from the contractile to the modified type is significantly retarded when the cells are grown on elastin coated dishes.

Until relatively recently, the primary methods available for securing a prosthetic material to tissue (or tissue to tissue) involved the use of sutures or staples. Fibrin glue, a fibrin polymer polymerized with thrombin, has also been used (primarily in Europe) as a tissue sealant and hemostatic agent.

Laser energy has been shown to be effective in tissue welding arterial incisions, which is thought to occur through thermal melting of fibrin, collagen and other proteins. The use of photosensitizing dyes enhances the selective delivery of the laser energy to the target site and permits the use of lower power laser systems, both of which factors reduce the extent of undesirable thermal trauma.

The present invention combines the advantages of tropoelastin-based products with the advantages of laser welding techniques, and provides a unique method of tissue repair and replacement. The invention makes possible tissue prostheses (particularly, vascular prostheses) that are essentially free of problems associated with prostheses known in the art.

Arterial replacement or reconstruction using tropoelastin based biomaterials not only may provide normal strength and elasticity but also may encourage normal endothelial re-growth, inhibit smooth muscle cell migration and thus restore normal vascular homeostasis to a degree not currently possible with synthetic grafts.

U.S. Pat. No. 4,589,882 is directed to a method for producing synthetic elastomeric polypeptide biomaterial which replicates a portion of the crosslinked tropoelastin polypeptide sequence. This synthetic elastomeric polypeptide biomaterial can be employed in repairing a natural elastic system of an animal body.

U.S. Pat. Nos. 4,721,096 and 4,963,489, which are incorporated herein by reference, disclose a three-dimensional cell culture system in which a living stromal tissue is prepared in vitro by a framework composed of a biocompatible, non-living material formed into a three dimensional structure having interstitial spaces. Collagen has been considered for a biodegradable biomaterials for use as a framework for a three-dimensional, multi-layer cell culture system (see U.S. Pat. No. 4,721,096 and No. 4,963,489).

An improved three-dimensional cell culture systems in which metabolic cycling optimizes the formation of extracellular matrix by cells grown on a three dimensional matrix is disclosed in U.S. Pat. No. 5,478,739 which is herein included as a reference. U.S. Pat. No. 5,478,739 reports production of collagens I, III, and IV, fibronectin, decorin, and non-sulfated glycosaminoglycans by cells in a three dimensional culture.

SUMMARY OF THE INVENTION

It is a general object of the invention to provide a method of effecting repair or replacement or supporting a section of a body tissue using tropoelastin, preferably crosslinked tropoelastin.

It is a specific object of the invention to provide a tropoelastin biomaterial suitable for use as a stent, for example, a vascular stent, or as conduit replacement, for example, as an artery, vein or a ureter replacement. The tropoelastin biomaterial itself can also be used as a stent or conduit covering or coating or lining.

It is a further object of the invention to provide a tropoelastin graft material suitable for use in repairing a lumen wall.

It is another object of the invention to provide a tropoelastin material suitable for use in tissue replacement or repair in, for example, interior bladder replacement or repair, intestine, tube replacement or repair such as fallopian tubes, esophagus such as for esophageal varicies, ureter, artery such as for aneurysm, vein, stomach, lung, heart such as congenital cardiac repair, or colon repair or replacement, or skin repair or replacement, or as a cosmetic implantation or breast implant.

It is also an object of the invention to provide a method of securing a tropoelastin biomaterial to an existing tissue with or without the use of sutures or staples.

Figure 1:
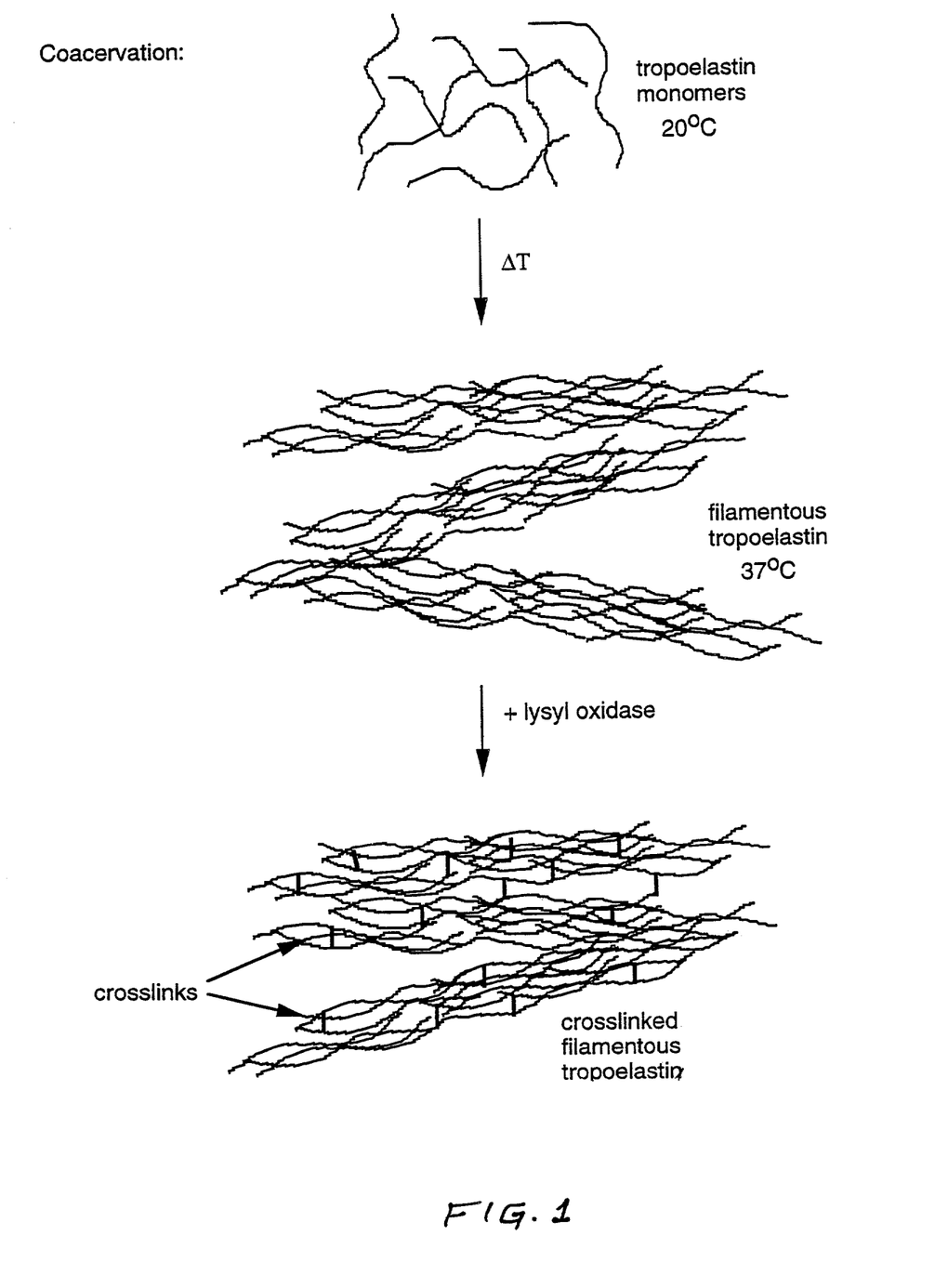
FIG. 1 is a schematic representation of a reaction of tropoelastin monomers for producing crosslinked tropoelastin.
Figure 2:
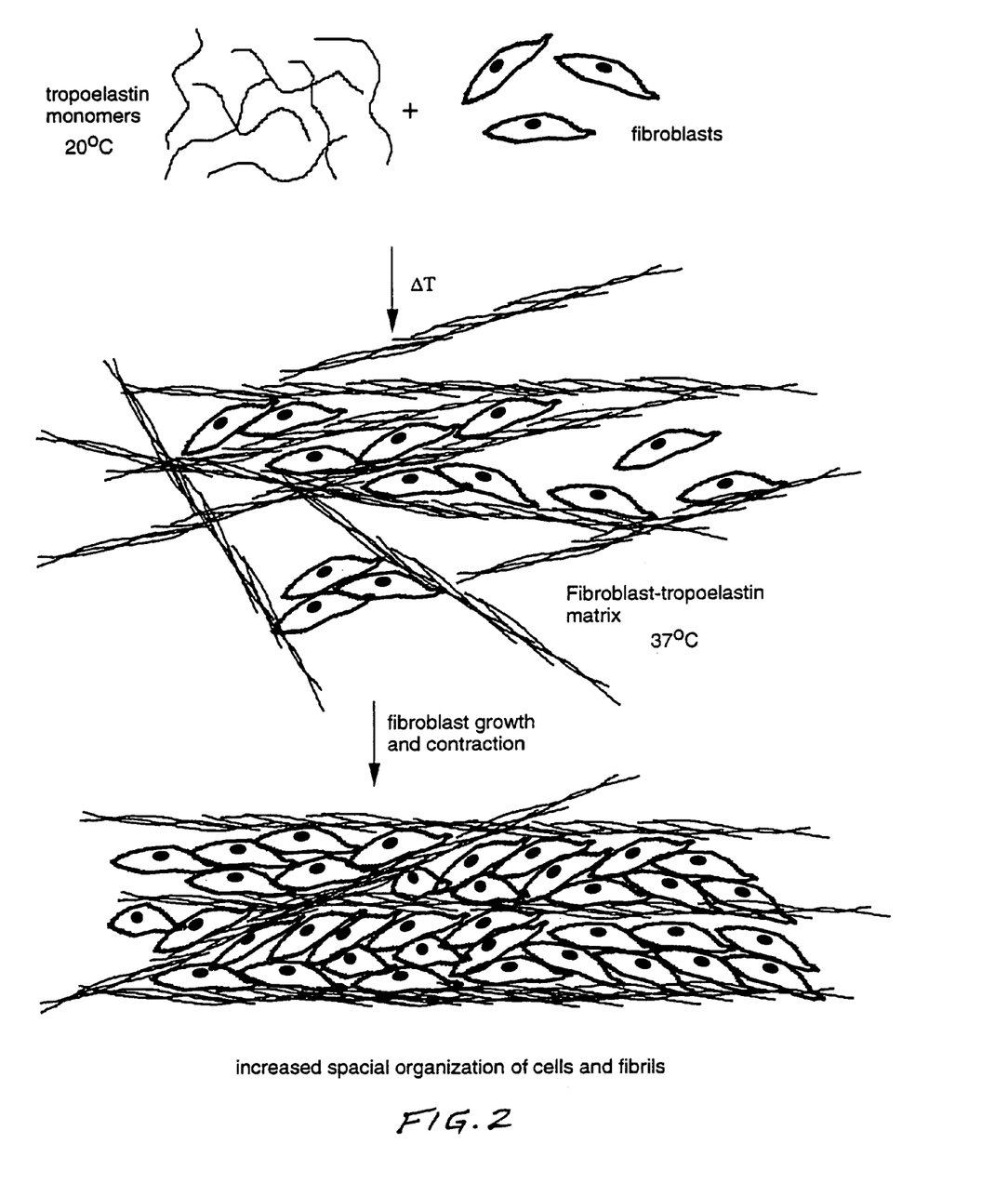
FIG. 2 is a schematic representation of a reaction of tropoelastin monomers in the presence of fibroblasts for producing crosslinked fibroblast-tropoelastin matrix.

The subject invention relates to method for using a tropoelastin polymer and for producing a tropoelastin biomaterial. Such methods comprise providing a tropoelastin monomer and then polymerizing same as hereinafter described. This will form a tropoelastin polymer which can be formed into a biocompatible tropoelastin biomaterial from said tropoelastin polymer for use in biomedical applications. For example, as shown in FIG. 1, the tropoelastin mononer can be formed into a filamentous structure by coacervation using moderating heating to effect same. Then, the filamentous tropoelastin is crosslinked using a crosslinking agent, such as lysyl oxidase, to form a crosslinked filamentous tropoelastin material. Finally, the tropoelastin polymer is formed into a layer of biocompatible tropoelastin biomaterial. It is this biocompatible tropoelastin biomaterial which can be used in the hereinafter described biomedical applications.

The subject invention provides a biocompatible, tropoelastin biomaterial formed into a three-dimensional structure. This structure can be used, for example, in a stromal support matrix populated with actively growing stromal cells. The stromal support matrix, which are preferably fibroblasts, can then be used to provide support, growth factors, and regulatory factors needed to sustain long-term active proliferation of cells in culture. A living stromal tissue can be prepared comprising stromal cells and connective tissue proteins naturally secreted by the stromal cells which are attached to and substantially enveloping a framework composed of a biocompatible, non-living material formed into three dimensional structure having interstitial spaces bridged by the stromal cells. The stromal cell systems contemplated herein are described in the following U.S. patents of Advanced Tissue Sciences, Inc. (formerly Marrow-Tech Incorporated), which are incorporated herein by reference:

U.S. Pat. No. 5,478,739, U.S. Pat. No. 5,460,939, U.S. Pat. No. 5,443,550, U.S. Pat. No. 5,266,480, U.S. Pat. No. 5,518,915, U.S. Pat. No. 5,516,681, U.S. Pat. No. 4,963,489, U.S. Pat. No. 5,032,508, U.S. Pat. No. 4,721,096, U.S. Pat. No. 5,516,680, U.S. Pat. No. 5,512,475, U.S. Pat. No. 5,510,254, and U.S. Pat. No. 5,160,490.

The tropoelastin structure can also have a cellular lining of human cells. The cells can be derived autologously, or otherwise, and formed into a lining on one of the major surfaces of the tropoelastin layer. Preferably, the cells which are employed to form such a lining are one endothelial cells and/or epithelial cells and/or urothelial cells.

The tropoelastin structure can also be formed into a biocompatible lining for mechanical structures to ensure their continued internal use in a human body. Examples of this are biocompatible linings for heart valves, heart implants, dialysis equipment, or oxygenator tubing for heart-lung by-pass systems.

The subject invention is directed to a method for producing a tropoelastin biomaterial, typically a crosslinked tropoelastin material, which is fused onto a tissue substrate, and the tropoelastin biomaterial itself. It is also directed to a method for using that tropoelastin biomaterial, a method for producing a tropoelastin biomaterial fused onto a tissue substrate, and a prosthetic device and a method of producing a prosthetic device including tropoelastin, The present invention also relates to a method of repairing, replacing or supporting a section of a body tissue using tropoelastin. The method comprises positioning tropoelastin at the site of the section and bonding the biomaterial to the site or to the tissue surrounding the site. The bonding is effected by contacting the biomaterial and the site, or tissue surrounding the site, at the point at which said bonding is to be effected, with an energy absorbing agent. The agent is then exposed to an amount of energy absorbable by the agent sufficient to bond the biomaterial to the site or to the tissue surrounding the site.

A tissue-fusible tropoelastin biomaterial can be produced using the method of the present invention which comprises a layer of tropoelastin biomaterial and a tissue substrate each having first and second outer surfaces, and an energy absorbing material applied to at least one of the outer surfaces. Preferably, the energy absorbing material penetrates into the biomaterial.

The energy absorbing material is energy absorptive within a predetermined range of light wavelengths depending on material thickness. The energy absorbing material is chosen so that when it is irradiated with light energy in the predetermined wavelength range, the intensity of that light will be sufficient to fuse together one of the first and second outer surfaces of the tropoelastin biomaterial and the tissue substrate. Preferably, the first and second outer surfaces of the tropoelastin biomaterial are major surfaces.

Typically, an energy absorbing material is indirectly irradiated by directing the light energy first through the tropoelastin biomaterial or tissue substrate and then to the energy absorbing material. Although the energy absorbing material can be applied directly to the tissue substrate, it is not the preferred method because of the difficulty in controlling penetration into the intertices of the tissue substrate.

In a preferred method of this invention, the energy absorbing material comprises a biocompatible chromophore, more preferably an energy absorbing dye. In one form of the present invention, the energy absorbing material is substantially dissipated when the tropoelastin biomaterial and the tissue substrate are fused together. In another form of this invention, the energy absorbing material comprises a material for staining the first or second surface of the tropoelastin biomaterial. The energy absorbing material can also be applied to one of the outer surfaces of the biomaterial by doping a separate elastin layer with an energy absorbing material and then fusing the doped separate elastin layer to the tropoelastin biomaterial. In any case, the energy absorbing layer is preferably substantially uniformly applied to at least one of the outer surfaces, typically in a manner wherein the energy absorbing material substantially covers the entire outer surface of the tropoelastin biomaterial.

Some of the key properties which effect the method of the present invention regarding fusing the tropoelastin biomaterial and tissue substrate include the magnitude of the wavelength, energy level, absorption, and light intensity during irradiation with light energy of the energy absorbing material, and the concentration of the energy absorbing material. These properties are arranged so that the temperature during irradiation with light energy for period of time which will cause fusing together of one of the first and second outer surfaces of the tropoelastin biomaterial and the tissue substrate is from about 40 to 140 degrees C., and more preferably from about 50 to 100 degrees C., but if well localized to the biomaterial tissue interface, can be as high as 600 degrees C. Furthermore, the average thickness of the energy absorbing material in the preferred method of this invention is from about 0.5 to 300 microns.

The subject invention is also directed to a prosthetic device comprising a support member comprising a stent, a conduit or a scaffold having a layer of tropoelastin material located on the support member. In the preferred case, the layer of the tropoelastin biomaterial completely surrounds the support member.

The support member of the prosthetic device is preferably formed of a metal or a synthetic material. The metal preferably comprises titanium, tantalum, stainless steel or nitinol. The synthetic material typically comprises a polymeric material. This polymeric material is generally selected from a group consisting of polyethylene terepthalate (Dacron), Gore-tex, teflon, polyolefin copolymer, polyurethane and polyvinyl alcohol. The support member can be formed from a hybrid polymer comprising a synthetic polymeric material and a natural polymeric material including fibrin and/or elastin. The support member can also be formed from a biological material, preferably from collagen.

The prosthetic device can comprise a layer of tropoelastin biomaterial. Preferably this layer comprises a covering, a coating, or a lining for the support member. The tropoelastin biomaterial can be formed by polymerization, or formed to a suitable size and shape by molding. The polymerized tropoelastin biomaterial can also be further cross-linked using gamma radiation and/or a cross-linking agent. In one form of the invention, the tropoelastin biomaterial is formed into a sheet, and the sheet is employed as the covering for the support. The sheet can also be attached to the support by grafting, by mechanical bonding, or by laser bonding.

The prosthetic device of this invention is implantable within a an artery, a vein, an esophagus, an intestine, a colon, a ureter, a liver, a urethra, or a fallopian tube.

A drug can be incorporated into the layer of tropoelastin material thereby decreasing the need for systemic intravenous or oral medications. Also, photodynamic therapy drugs ("PTD") which are activated with light can be employed herein.

In use, a method for producing the prosthetic device of the present invention comprises first providing a layer of tropoelastin biomaterial and a support member comprising a stent, a conduit or a scaffold. Then, the layer of tropoelastin biomaterial is applied to the support member to form the prosthetic device. For example, a layer of tropoelastin material can be located on the support member and can be fused together. This can be accomplished by applying an energy absorbing material, which is energy absorptive within a predetermined range of light wavelengths, to the tropoelastin biomaterial in an amount which will cause fusing together thereof. Thus, the energy absorbing material is irradiated with light energy in the predetermined wavelength range with an intensity sufficient to fuse together the tropoelastin biomaterial on said support member thereby fusing together the tropoelastin biomaterial on the tissue substrate.

Further objects and advantages of the invention will be clear from the description that follows.

DETAILED DESCRIPTION OF THE INVENTION

Monomer Synthesis

Tropoelastin monomer is the soluble biosynthetic precursor to elastin. It is formed naturally in vetebrates. Tropoelastin can be isolated from the aortas of copper deficient swine by known methods such as described by E. B. Smith, Atherosclerosis 37 1980) tropoelastin is a 72-kDa polypeptide which is rich in glycine, proline, and hydrophobic amino acids. The exact amino acid composition of tropoelastin differs from species to species. Any polypeptide moiety that has art-recognized homology to tropoelastin can be considered a tropoelastin monomer for the invention.

The tropoelastin can be isolated from mammalian tissue or produced using recombinant expression systems. Furthermore, tropoelastin splice variants from any species can also be used for the invention.

The following are exemplary descriptions of methods of producing tropoelastin monomers used in the invention:

1. Tropoelastin can be extracted from mammals which have been placed on copper deficient or lathyritic diets. The deficiency of copper in the mammalian diet inhibits lysyl oxidase resulting in the accumulation of tropoelastin in elastin rich tissues. Copper deficient animals are grown rapidly on a diet composed largely of milk products and must be kept isolated from contaminating sources of copper. The protocol for raising copper deficient swine is detailed by L. B. Sandberg and T. B. Wolt. Production of Soluble Elastin from Copper Deficient Swine. Methods in Enzymology 82 (1982) 657–665. 150 mg of tropoelastin can be extracted from a 15-kg copper-deficient swine.

2. In a method similar to copper deficiency method in No. 1 above, feeding animals chemicals that effectively inhibit the action of lysyl oxidase (lathyrogens) also restricts the conversion of tropoelastin to amorphous elastin. This method produces similar yields of tropoelastin to copper-deficient swine. However, the special cages, water and diet required to raise copper-deficient animals are not required herein. To induce lathyrisim, animal diets are supplemented with 0.1% by weight a-aminoacetonitrile-HCl and 0.05% a-aminocaproic acid as described by Celeste B. Rich and Judith Ann Foster, Isolation of Soluble Elastin-Lathyrism. Methods in Enzymology 82 (1982) 665–673.

3. Tropoelastin can also be produced by mammalian cell culture systems. Short term cultivation of bovine vascular endothelial cells, nuchal ligament fibroblasts from cows and sheep, human skin fibroblasts, and vascular smooth muscle cells from pigs and rabbits results in the accumulation of tropoelastin in the culture medium.

4. Recombinant tropoelastin produced by a protein expression system is the preferred monomer for the invention. Recombinant protein technology is the transfer of recombinant genes into host organisms that grow and convert nutrients and metabolites into recombinant protein products. Using this technology, cDNA encoding tropoelastin can be cloned and expressed in protein expression systems to produce biologically active recombinant tropoelastin. Functionally distinct hydrophobic domains and lysine rich crosslinking domains are encoded in separate exons. This existence of multiple splice variants of tropoelastin in several species can be attributed to Cassette-like alternative splicing of elastin pre-mRNA. Expression of different recombinant splice variants of tropoelastin can produce proteins with distinct qualities. In addition, site directed in vitro mutagenesis can be used to alter the polypeptide sequence of the naturally occurring gene, thus creating alternate polypeptides with improved biological activity and physical properties. Expression of the full length elastin cDNA clone, cHEL2 and subsequent purification of recombinant human tropoelastin (rTE) has been achieved by Joel Rosenbloom, William R. Abrams, and Robert Mecham. Extracellular Matrix 4: The Elastic Fiber. The Faseb Journal 7 (1993) 1208–1218. rTE produced by the methods of Rosenbloom et. al. can be used for the invention, however, the methods are not considered to be part of the present invention. In addition, the invention is not limited to rTE produced from the expression of cHEL2. rTE produced from the expression of any tropoelastin genomic or cDNA can be used for the invention.

To help overcome the moderate yields of rTE recovered by Rosenbloom and colleagues, Martin, Vrhovski and Weiss successfully synthesized and expressed a gene encoding human tropoelastin in E. Coli. In constructing the gene they tailored the rare codon bias of the synthetic sequence to match the known preferences of E. Coli. rTEtropoelastin produced by expression of synthetic genes can be used for the invention.

rTE is used in the invention can be produced in non-bacterial expression vector systems. Yeast expression vector systems are well suited for expressing eukaryotic proteins and tropoelastin is a potentially excellent candidate for expression in yeast.

For large scale heterologous gene expression, the baculovirus expression vector system (BEVS) is particularly advantageous. BEVS has several advantages over other expression systems for mammalian gene expression. It is safer, easier to scale up, more accurate, produces higher expression levels, and is ideal for suspension cultures permitting the use of large-scale bioreactors. Generation of a recombinant baculovirus particle carrying a clone of elastin cDNA coding for an isoform of tropoelastin is achieved through homologous recombination or site specific transposition and is followed by recombinant baculovirus infection of insect cells (Sf9 or High Five) and subsequent recombinant gene expression as follows:

Elastin cDNA encoding tropoelastin is identified and isolated from a cDNA library. The gene is cloned into a pFastBac or pFastBac HT donor plasmid using standard restriction endonucleases and DNA ligase. Correct insertion of gene is verified by restriction endonuclease digestion and PCR analysis. The DNA is then transformed into DH10Bac cells which harbor a bacmid a mini-attTn7 target site and a helper plasmid. Once cloned into the DH10Bac cells, the elastin gene undergoes site-specific transposition into the Bacmid. Transposition results in the disruption of a LacZalpha gene and colonies containing recombinant bacmids are white. High molecular weight mini-prep DNA is prepared from selected *E. Coli* clones containing the recombinant bacmid and is used to transfect SF9 or High Five insect cells using CellFECTIN reagent. The insect cells produce actual baculovirus particles harboring the tropoelastin encoding gene. The virus particles are harvested and are subsequently used to infect insect cells which produce high yields of the recombinant protein product, tropoelastin.

Tropoelastin accumulated in elastin rich tissues by the inhibition of lysyl oxidase through copper deficiency or lathyrism can be isolated by exploiting tropoelastin's high solubility in short-chain alcohols. Modified methods of this alcohol extraction procedure can be used to purify rTE from expression hosts such as bacteria, yeast, insect, and mammalian cells in culture. Methods have been described in detail which involve precipitation of tropoelastin with n-propanol and n-butanol. Tropoelastin expressed in insect cells using the pFastBac HT baculovirus expression system (Life Technologies, Gaithersburg, Md.) can be purified in a single affinity chromatography step with Ni—NTA resin. The invention is not limited to any particular method of tropoelastin isolation or purification.

Polymer Synthesis

In tissue, tropoelastin is naturally crosslinked by several tetra and bifunctional cross-links to form elastin. These crosslinks arise through the oxidative deamination and condensation of lysyl side chains. Both bifunctional lysinonorleucine and allysine aldol and tetrafunctional desmosine crosslinks are formed. Tetrafunctional desmosine crosslinks are a distinguishing feature of elastin. Tropoelastin can be converted to a tropoelastin biomaterial by oxidative deamination of lysyl residues and the subsequent crosslinking of the monomeric moiety catalyzed by the copper dependent enzyme lysyl oxidase (protein-lysine 6-oxidase).

A primary purpose of the invention is to produce cross-linked elastic matrices that are identical to or closely mimic those found naturally in elastic tissue. It is, therefore; advantageous to crosslink tropoelastin monomers with the same bifunctional and tetrafunctional cross-links found in elastin. However, the invention is not limited to these naturally occurring cross-links and any type of cross-link formed between tropoelastin monomers, whether produced chemically, enzymatically or radiatively, can be used for the invention.

Crosslinking tropoelastin with lysyl oxidase will produce matrices that closely resemble or imitate naturally occurring ones. Lysyl oxidase (protein-lysine 6-oxidase) catalyzes the oxidation of lysine residues to a peptidyl α-aminoadipic -α-semialdehyde. This aldehyde residue spontaneously condenses with neighboring aldehydes or α-amino groups forming interchain or intrachain crosslinkages (Kagan, 1991). Lysyl oxidase from any source can be used so long as the tropoelastin it is intended to oxidize is a suitable ligand. Lysyl oxidase is typically extracted from bovine aorta and lung, human placentas, and rat lung with 4 to 6 M urea extraction buffers. Recombinantly produced lysyl oxidase can also be used to cross-link tropoelastin. Recombinant tropoelastin (rTE26A) has been cross-linked with lysyl oxidase in 0.1 M sodium borate, 0.15 M NaCl, pH 8.0 when incubated for 24 hr at 37° C. (Bedell-Hogan, 1993). Another preferred method of crosslinking tropoelastin is with γ-irradiation. γ-irradiation causes formation of free radicals which can result in crosslink formation. 20 mrad of γ-irradiation has been shown to crosslink an elastin like polypeptide, poly(GLy-Val-Gly-Val-Pro), into an elastomeric matrix and has increased the elasticity and strength of a elastin-fibrin biomaterial. The addition of chemical agents that form crosslinks when activated with irradiation can also be used. Sulfur derivatives combined with γ-irradiation has been shown to further increase the strength of an elastin-fibrin biomaterial. Chemical crosslinking reagents such as glutaraldelhyde may also be used to cross-link tropoelastin matrices.

A preferred method of organizing tropoelastin monomers into fibrous structures prior to cross-linking is by taking advantage of the property of coacervation exhibited by tropoelastin. Tropoelastin is soluble in water at temperatures below 37° C., however, upon raising the temperature to 37° C. tropoelastin aggregates into a filamentous structure called a coacervate. Formation of tropoelastin coacervates may be a natural step prior to cross-link formation during elastogenesis in tissue. Coacervated tropelastin can be crosslinked by lysyl oxidase under the appropriate conditions to produce filamentous elastin fibrils. Alignment may be facilitated by exposure of the tropoelastin coacervates to a magnetic field prior to crosslinking.

Collagen is the major structural polymer of connective tissues. Artificial collagen fibers have been produced from soluble collagen I extracts. Fibers such as these can be formed into scaffoldings onto which tropoelastin can be cross-linked into amorphous insoluble elastin producing a elastin/collagen composite (see FIG. 3). The collagen fibers lend form and tensile strength to the tropoelastin material and the crosslinked tropoelastin fibrils lend elasticity thus creating a composite material that very nearly approximates naturally occurring connective tissue.

Proteoglycans are major constituents of the extracellular matrix. The addition of Hyaluronic acid, dermatan sulfate, keratane sulfates, or Chondroitin sulfates as co-materials may further the strength and cohesion of the material. In addition, cell function is in part controlled by the extracellular matrix. Fibronectin, vitronectin, laminin nad collagen, as well as various glycosaminoglycans all mediate cell adhesion. Fibronectin has several roles in the connective tissue matrix. It has an organizing role in developing tissues and it plays a major role in cell adhesion to the extracellular matrix. Incorporation of fibronectin as a co-material may improve the cell adhesion properties of the tropoelastin based biomaterial. Microfibrils are distributed throughout the body, and are prevalent in elastic tissues and fibers. The presence of microfibrils during polymerization of tropoelastin monomers may help to organize monomers yielding a material with improved structural organization. Also, microfibrils are known to sequester calcium ions and are thought to play a role in protecting tropoelastin from chronic calcification.

Product Synthesis

The utility of tropoelastin based biomaterials may be further improved by combining them with synthetic or natural polymer co-materials, forming composites, and by adding bioactive impregnates.

Antibiotics and/or anticoagulants or other agents can be added to the tropoelastin matrix providing localized drug therapy and preventing infection. In surgical repair of abdominal traumatic injuries, infection represents a major problem particularly when vascular prosthetic implants are used. An tropoelastin graft with antibiotic incorporation may be ideal because it avoids sacrifice of an autologous artery or vein which decreases surgical time and precludes the necessity to use synthetic prosthetic materials which may be more prone to infection than tropoelastin grafts. Bioactive impregnates may also include anti-coagulants (Hirudin), coagulants, anti-proliferative drugs (Methatrexate), growth factors, anti-virals, and anti-neoplastics.

Small diameter vascular grafts fail at an unacceptable rate due to their inherent thrombogenicity. This problem may be decreased by the deposition of a living autologous endothelial cell lining. Autologous endothelial cell transplantation can accelerate the formation of an immunologically compatible; complete endothelial lining using microvascular endothelial cells derived from the adipose tissue of a recipient animal (Jarrell, et al.) In the porcine model the peritoneal fat had been determined to be optimal for this purpose due to the predominance of microvascular and endothelial cells. Following extraction of peritoneal fat, homogenization, collagenase digestion, and centrifugal separation, cells are expeditiously transplanted onto the luminal surface of crosslinked tropoelastin vascular grafts using an intra-operative isolation technique combined with the rapid pressure sodding techniques described by Jarrell and Williams.

The present invention constitutes a three dimensional matrix made of elastin or tropoelastin for use as a framework for a three-dimensional, multi-layer cell culture system. Populating endogenous biologic materials such as a tropoelastin matrix with stromal cells is preferable to populating matrices made of synthetic biocompatible, non-living materials. Synthetic biodegradable biomaterials must undergo enzyme catalyzed degradation or spontaneous hydrolysis in order to avoid permanent chronic foreign body reactions. On the contrary, elastin is a naturally occurring protein in the extracellular matrix of many tissues and, therefore, does not illicit a foreign body reaction. Unlike collagen, elastin undergoes very little post-developmental remodelling or breakdown and is a relatively permanent connective tissue structure during the life of an organism. Tropoelastin biomaterials can provide a relatively permanent, natural support matrix for three dimensional cell cultures that when implanted acts as a template for reconstruction of the organs and tissues. In addition the longevity and integrity of implanted tropoelastin is regulated in response to the biological needs of the tissue rather than environmentally induced hydrolysis or enzymatic degradation of a foreign substance.

Elastin structures constituting a framework for a three-dimensional, multi-layer cell culture system will provide intact elastic structures not constructed by stromal cells populating synthetic matrices. In vivo elastin production is thought to only occur during development and ceases during childhood (the only exceptions being hypertension and restenosis). Elastogenesis is a complex method and formation of mature elastic structures not likely to be achieved in relatively simple in vitro cell culture systems. However, it has not been reported that such three dimensional cell culture systems can organize elastin into coherent fibrous matrices analogous to those found in elastic tissues. A method by which to produce a living tissue graft with elastic structure and function most similar to tissue which is high in elastin content is by culturing cells in three dimensional frameworks made of elastin or elastin based biomaterials. This insures the presence of biologically important elastic structures in the living tissue grafts.

A method for both organizing tropoelastin fibrils and providing a support for fibroblast growth is by coacervating tropoelastin monomers in solution with fibroblasts. Tropoelastin monomers mixed with stromal cells (fibroblasts) in a physiologic buffer aggregate into fibers (coacervation) upon raising the temperature of the solution to 37° C. In doing so the fibroblasts become trapped in a loose matrix of elastic fibers. The tropoelastin fibers can be crosslinked either by including lysyl oxidase in the buffer or a temperature sensitive recombinant form of lysyl oxidase that, for example, is inactive at 20° C. and active at 37° C. or by culturing the tropoelastin-fibroblast matrix in such a manner that the fibroblasts secrete natural lysyl oxidase into the coacervate matrix. The contraction of the fibroblasts bound to the coacervated tropoelastin monomers could preferentially align the tropoelastin fibrils prior to crosslinking.

Sterilization

The tropoelastin biomaterial of the invention is normally secured to existing tissue. Various techniques for effecting that attachment can be used, including art-recognized techniques, including suturing, staples and gluing. However, in some cases it is preferred that the biomaterial be secured using a tissue welding energy source and an agent that absorbs energy emitted by that source. Advantageously, the energy source is an electromagnetic energy source, such as a laser, and the absorbing agent is a dye having an absorption peak at a wavelength corresponding to that of the laser. The tropoelastin biomaterial and the tissue to be welded have much less absorption of light at this wavelength and the effect therefore is confined to a zone around the dye layer. A preferred energy source is a laser diode having a dominant wavelength at about 808 nm and a preferred dye is indocyanine green (ICG), maximum absorbance 795–805 nm (see WO 91/04073). Other laser/dye combinations can also be used. It is preferred that the dye be applied to that portion of the biomaterial that is to be contacted with and secured to the existing tissue. The dye can also be applied to the surface of the structure to which the tropoelastin biomaterial is to be welded or secured. The dye can be applied directly to the biomaterial or the surface of the biomaterial can first be treated or coated (eg primed) with a composition that controls absorption of the dye into the biomaterial so that the dye is kept as a discrete layer or coating. Alternatively, the dye can be bound to the troptropoelastin biomaterial so that it is secured to the surface and prevented from leeching into the material. The dye can be applied in the form of a solution or the dye can be dissolved in or suspended in a medium which then can be applied as a thin sheet or film, preferably, of uniform thickness and dye concentration.

Tissue welding techniques employing a soldering agent can be used. Such techniques are known (WO 91/04073). Any proteinaceous material that thermally denatures upon heating can be used as the soldering agent (for example, any serum protein such as albumin, fibronectin, Von Willebrand factor, vitronectin, or any mixture of proteins or peptides). Solders comprising thrombin polymerized fibrinogen are preferred, except where such materials would cause undesirable thrombosis or coagulation such as within vascular lumens. Solders are selected for their ability to impart greater adhesive strength between the biomaterial and the tissue. The solder should be non-toxic and generally biocompatible.

In accordance with the present invention, the laser energy can be directed to the target site (eg, the dye) directly from the laser by exposure of the tissue (eg, during a surgical procedures). In some cases, i.e. endovascular catheter-based treatments where open surgical exposure does not occur, the laser energy is directed to the bonding site via optical fibers. When ICG is used as the dye, targeting media wavelengths of around 800 nm can be used. Such wavelengths are not well absorbed by many tissues, particularly blood and vascular tissues, therefore, there will be a negligible effect on these tissues and thermal effects will be confined to the dye layer. The biomaterial of the invention similarly has little optical absorbance in this waveband, as compared to the energy absorbing dye. Thus, the laser energy can pass through either the biomaterial or the native tissue and be absorbed by the dye layer as shown in FIG. 1. Once the surgeon has exposed the surface or vessel where the biomaterial reinforcement or replacement is to be effected, the dye-containing surface of the biomaterial is placed in contact with the native tissue at the site and laser energy delivered by directing the laser beam to the desired location. The absorbance of the dye (eg ICG) layer is ideally previously or concurrently determined so that the optimal amount of light for optimal bonding can be delivered. Pressure can be used to ensure adequate approximation of the tissue and biomaterial. With a diode laser source, the diode laser itself, or a condenser or optical fiber based optical delivery system, can be placed against the material to ensure uniform light delivery.

In cases where a new elastin lining or new-internal elastic lamina is required, for example, following an open surgical endarterectomy, once the artery has been surgically cleared of the atheroma or other lesion, the biomaterial is then put in place, dye side down. The biomaterial can be deployed as a flat patch or as a tubular segment. A tubular segment can be hollow or filled with a material that supports the lumen during placement and that is melted with low grade heat or dissolved or removed with a variety of means. When necessary, a small number of surgical sutures (eg stay sutures) can be used to appose the edges of the vessel together or to sew the vessel. Once the biomaterial is in place, the laser energy is directed through the vessel wall or through the biomaterial to the absorbing dye, the appropriate laser energy having been previously determined based-upon the measured absorbance in the biomaterial. Alternatively, the dye can be applied at the time of the surgery to the biomaterial or the vessel wall or both and then laser energy delivered. In this embodiment, absorbance can be determined at the time of the surgery to the biomaterial or the vessel wall or both and then laser energy delivered or with a feedback device that assesses the adequacy of the bonding or thermal effect.

Figure 3:
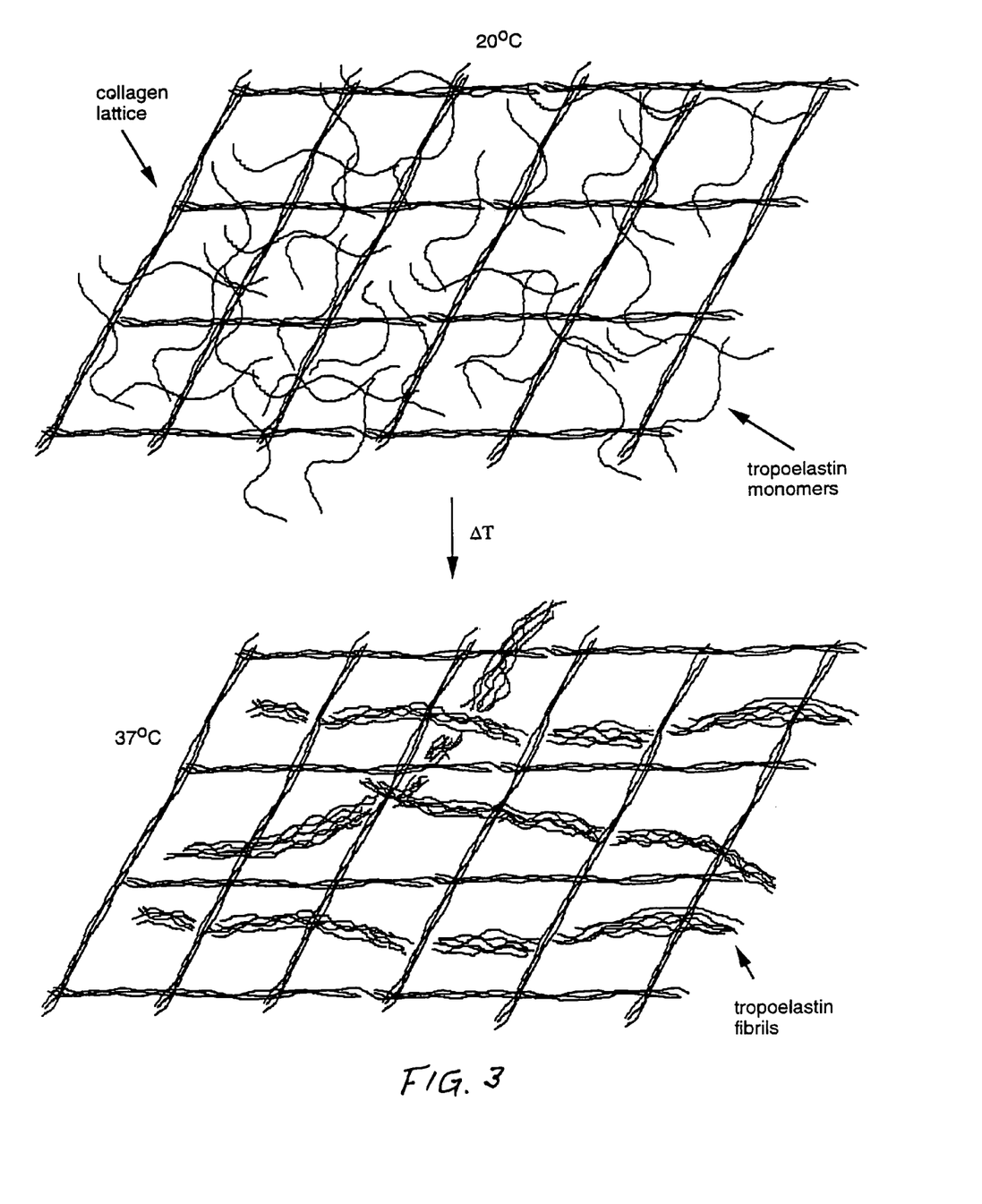
FIG. 3 is a schematic representation of a reaction of tropoelastin monomers in the presence of a preformed collagen lattice for producing tropoelastin fibrils supported on the collagen latice structure.

In addition to the above, the biomaterial of the invention can be used as a patch material for use in intestinal or colon repairs which frequently do not heal well with current techniques, particularly when the patient has nutritional or other problems or when the patient is in shock, such as in the case of multiple gunshot wounds or other abdominal injuries (see FIG. 3). The use of such a patch can, for example, seal off intestinal contents and thereby reduce the likelihood of peritonitis. In addition, a patch can be used on a solid organ, such as the liver or lung, when lacerations have occurred. Similarly, the biomaterial of the invention can be used to repair or replace portions of the urinary system i.e., from the calyces of the kidney on down to the urethra. The patch can also be used to seal a defect in a cardiac chamber, such as an atrial septal defect, as well as bronchial or rectal fistulas. The biomaterial can also be used as a cerebrovascular patch for an aneurysm. The biomaterial can be sealed in place with targeted laser fusion. For applications where direct exposure is not possible or not desirable, a variety of catheter or endoscopic systems can be employed to direct the laser energy to the target site bio-materials to which the invention relates can be used in a variety of other clinical and surgical settings to effect tissue repair graft. For delivery of biomaterial in the form of an intravascular stent, the biomaterial can be pre-mounted upon a deflated balloon catheter. The balloon catheter can be maneuvered into the desired arterial or venous location using standard techniques. The balloon can then be inflated, compressing the stent (tropoelastin biomaterial) against the vessel wall and then laser light delivered through the balloon to seal the stent in place (the dye can be present on the outside of the biomaterial). The balloon can then be deflated and removed leaving the stent in place. A protective sleeve (of plastic or the like) can be used to protect the stent during its passage to the vessel and then withdrawn once the stent is in the desired location.

The biomaterial of the invention can also be used as a biocompatible covering for a metal or synthetic scaffold or stent. In such cases, simple mechanical deployment can be used without the necessity for laser bonding. Laser bonding can be employed, however, depending upon specific demands, eg, where inadequate mechanical bonding occurs, such as in stent deployment for abdominal aortic aneurysms. An alternative catheter-based vascular stent deployment strategy employs a temporary mechanical stent with or without a balloon delivery device.

A further catheter-based vascular stent deployment strategy employs a heat deformable metal (such as nitinol or other similar type metal) scaffold or stent or coating that is incorporated into the catheter tubing beneath the stent biomaterial. The stent is maneuvered into the desired location whereupon the deformable metal of the stent is activated such that it apposes the stent against the vessel wall. Laser light is then delivered via an optical fiber based system, also incorporated into the catheter assembly.

The tropoelastin-based biomaterial can also be used to replace portions of diseased or damaged vascular or nonvascular tissue such as esophagus, pericardium, lung plura, etc. The biomaterial can also be used as a skin layer replacement, for example, in burn or wound treatments. As such, the biomaterial serves as a permanent dressing that acts as a scaffolding for epithelial cell regrowth. The biomaterial can include antibiotics, coagulants or other (drugs desirable for various treatments that provide high local concentrations with minimal systemic drug levels. The tropoelastin biomaterial can be deployed with a dye on the tissue side and then fused with the appropriate wavelength and laser energy.

In addition to repair of tubular body structures, the biomaterial of the present invention can also be used in organ reconstruction. For example, the biomaterial can be molded or otherwise shaped as a pouch suitable for use in bladder reconstruction. The biomaterial of the invention can also be molded or otherwise shaped so as to be suitable for esophageal replacement. Again, metal or synthetic mesh could also be associated with the implant if extra wall support is needed so as to control passage of food from the pharynx to the stomach. This could be used for stenosis of the esophagus, repair from acid reflux for erosive esophagitis or, more preferably, for refurbishing damaged esophageal segments during or following surgery or chemotherapy for esophageal carcinoma.

For certain applications, it may be desirable to use the biomaterial of the invention in combination with a supporting material having strong mechanical properties. For those applications, the biomaterial can be coated on the supporting material (see foregoing stent description), for example, using the molding techniques described herein. Suitable supporting materials include polymers, such as woven polyethylene terepthalate (Dacron), teflon, polyolefin copolymer, polyurethane polyvinyl alcohol or other polymer. In addition, a polymer that is a hybrid between a natural polymer, such as fibrin and elastin, and a non-natural polymer such as a polyurethane, polyacrylic acid or polyvinyl alcohol can be used (see Giusti et al, Trends in Polymer Science 1:261 (1993). Such a hybrid material has the advantageous mechanical properties of the polymer and the desired biocompatibility of the tropoelastin material. Examples of other prostheses that can be made from synthetics (or metals coated with the tropoelastin based biomaterial or from the biomaterial/synthetic hybrids include cardiac valve rings and esophageal stents.

The tropoelastin-based prostheses of the invention can be prepared so as to include drug; that can be delivered, via the prostheses, to particular body sites. For example, vascular stents can be produced so as to include drugs that prevent coagulation, such as heparin, or antiplatelet drugs such as hirudin, drugs to prevent smooth muscle ingrowth or drugs to stimulate endothelial damaged esophageal segments during or following surgery or chemotherapy for esophageal carcinoma or endothelial regrowth. Vasodilators can also be included.

Prostheses formed from the tropoelastin bio-material can also be coated with viable cells, cells from the recipient of the prosthetic device. Endothelial cells, preferably autologous (eg harvested during liposuction), can be seeded onto the elastin bioprosthesis prior to implantation (eg for vascular stent indications). Alternatively, the tropoelastin biomaterial can be used as a skin replacement or repair media where cultured skin cells can be placed on the biomaterial prior to implantation. Skin cells can thus be used to coat elastin biomaterial.

All documents cited above are hereby incorporated in their entirety by reference. One skilled in the art will appreciate from a reading of this disclosure that various changes in form and detail can be made without departing from the true scope of the invention.

We claim:

1. A method for producing a biomaterial, which comprises:
   providing a monomer consisting essentially of tropoelastin;
   polymerizing said monomer to form a polymer consisting essentially of tropoelastin;
   forming a biocompatible biomaterial consisting essentially of tropoelastin from said polymer; and
   forming a three-dimensional support structure wherein said biomaterial is combined with a stromal support matrix populated with actively growing stromal cells.

2. The method of claim 1, wherein the stromal support matrix comprises fibroblasts.

* * * * *